(12) United States Patent
Zhao (10) Patent No.: US 11,145,556 B2
(45) Date of Patent: Oct. 12, 2021

(54) METHOD AND DEVICE FOR INSPECTION OF SEMICONDUCTOR SAMPLES

(71) Applicant: Carl Zeiss SMT GmbH, Oberkochen (DE)

(72) Inventor: Si Ping Zhao, Singapore (SG)

(73) Assignee: Carl Zeiss SMT GmbH, Oberkochen (DE)

( * ) Notice: Subject to any disclaimer, the term of this patent is extended or adjusted under 35 U.S.C. 154(b) by 139 days.

(21) Appl. No.: 16/690,952

(22) Filed: Nov. 21, 2019

(65) Prior Publication Data

US 2021/0159126 A1  May 27, 2021

(51) Int. Cl.
| | |
|---|---|
| *H01L 21/66* | (2006.01) |
| *H01L 21/306* | (2006.01) |
| *B24B 37/005* | (2012.01) |
| *G01N 23/22* | (2018.01) |
| *H01L 21/67* | (2006.01) |
| *G01N 33/00* | (2006.01) |

(52) U.S. Cl.
CPC ............ *H01L 22/12* (2013.01); *B24B 37/005* (2013.01); *G01N 23/22* (2013.01); *H01L 21/30625* (2013.01); *H01L 21/67288* (2013.01); *G01N 2033/0095* (2013.01)

(58) Field of Classification Search
None
See application file for complete search history.

(56) References Cited

U.S. PATENT DOCUMENTS

| | | | |
|---|---|---|---|
| 2008/0070483 A1* | 3/2008 | Roettger | B24B 37/08 451/37 |
| 2013/0316521 A1* | 11/2013 | Sasaki | H01L 21/02024 438/478 |
| 2016/0193711 A1* | 7/2016 | Tanaka | B24B 49/12 451/5 |

\* cited by examiner

*Primary Examiner* — Dung A. Le
(74) *Attorney, Agent, or Firm* — Fish & Richardson P.C.

(57) ABSTRACT

A method and device for inspection or analysis of a semiconductor sample is provided. The method includes: sandwiching a processed semiconductor sample between two blocks of a semiconductor material; polishing the sandwiched sample such that an even surface is obtained; and measuring the surface of the sandwiched sample. The blocks of a semiconductor material comprise the same semiconductor material as the semiconductor sample.

19 Claims, 6 Drawing Sheets

METHOD AND DEVICE FOR INSPECTION OF SEMICONDUCTOR SAMPLES

FIELD

The present application relates to semiconductor inspection sample preparation methods and devices. In some embodiments, this application relates to cross sectional analysis of processed semiconductors.

BACKGROUND

Current state-of-the-art semiconductor devices are often built with minimum structure sizes or Critical Dimensions (CD) of down to about 5 nanometers, and devices with smaller critical dimensions are being developed. The fabrication of such semiconductor devices, depending on the type of device, may involve about 1000 fabrication steps, starting with a blank wafer, to form the semiconductor devices on the wafers. These fabrication steps include for example about 100 lithography steps. In modern manufacturing lines, up to 200 wafers may pass each lithography step by hour.

In order to obtain a high yield of semiconductor devices of close to 100%, it is often desirable to closely monitor variations in any fabrication step that may indicate process variations leading to defects. Therefore, high speed in-line metrology is commonly used between different fabrication steps or is integrated into the fabrication steps. This metrology is sometimes also calls wafer inspection. Wafer inspection tools are used to detect indications of process variations or defect candidates within a structure after specified fabrication steps. Typical silicon wafers used in manufacturing of semiconductor devices have diameters of up to 12 inches (300 mm). With the small structure sizes mentioned above, defect candidates of the order of the critical dimensions are desirably identified in a very large area in a short time.

For wafer inspection, cross-sectional analysis can be used in which a sample is cut out from a semiconductor and the prepared sample is subjected to analysis methods such as scanning electron microscopy (SEM) methods.

In this respect, the electron-microscope image distortion generated by electromagnetic interference (EMI) is an issue for accurate imaging in scanning electron microscopy. Available commercial ways of addressing this issue may utilize sophisticated hardware for EMI detection and compensation. The efficiency of those approaches can depend on the complexity of distortions influence on SEM system. Selection of a proper method for reduction of the distortions is crucial. The current investigations allowed for a separation of the distortions can impact on several components of SEM system. A sum of signals from distortion sources can cause wavy deformations of specimen shapes in SEM images. The separation of various reasons of the distortion is usually based on measurements of the periodic deformations of the images for different electron beam energies and working distances between the microscope final aperture and the specimen. In particular, when the SEM beam energy is less than 400 eV, the non-uniform distribution of surface potential due to edge effect would deflect the beam and can lead to the distortion issue.

SUMMARY

According to an embodiment, a method for inspection or analysis of an exposed semiconductor sample is provided, including: sandwiching a processed semiconductor sample between two blocks of a semiconductor material; polishing the sandwiched sample such that an even surface is obtained; and measuring at the polished surface of the sample, wherein the blocks of a semiconductor material include the same semiconductor material as the semiconductor sample.

A processed semiconductor sample as used herein may refer to a processed wafer, to a partially processed or fully processed wafer, or, in other words, a wafer in any stage during or after the front-end processing of the wafer. The wafer may be a semiconductor wafer, in particular a Si wafer or GaAs wafer, a SOI wafer, or a part thereof. The semiconductor sample may have been exposed in a photolithography process.

The inspection can be one or more of an inspection during a wafer production process, at-line inspection during a wafer production process, preparation, calibration, or inspection at any point of wafer production. This method is particularly applicable for laboratory analysis for Si devices and/or wafers. In particular, the method is applicable for coupon level or test coupon samples. The coupon can be a wafer coupon. In general, a coupon is a device portion used to test the quality of a device fabrication process, in this case a process for producing semiconductor devices. Test coupons are fabricated on the same wafer as the devices, for example at the edges. Coupons are then inspected to ensure proper layer alignment, electrical connectivity, and cross sectioned to inspect internal structures. Such setup is useful for development of new devices and/or during production of novel devices.

The surface of the semiconductor sample may include the side surface of the semiconductor sample. The semiconductor sample may be sandwiched with the exposed side on the side facing one of the blocks. The side surface may be the shortest side of the semiconductor sample. Moreover, the side surface may face one of the blocks of a semiconductor material. A common sample is a piece of a processed Si wafer. This thin piece can be sandwiched between two blocks.

Sandwiching a processed semiconductor sample may include fixing the sample between the two blocks of semiconductor material, fixing the processed semiconductor sample between the two blocks of a semiconductor material using an adhesive, or fixing the processed semiconductor sample between the two blocks of a semiconductor material using a suitable adhesive. The adhesive may be one or more of an adhesive or glue-like adhesive, or an epoxy adhesive.

The blocks of a semiconductor material may be larger in size than the semiconductor sample. In an embodiment, the thickness of each block of semiconductor material sandwiching the semiconductor sample may be about 5 mm, about 6 mm, or in a range of 5-10 mm.

Measuring the surface of the sandwiched sample may include measuring by multi-beam scanning electron microscopy. Multi-beam scanning electron microscopy may include Delta SEM.

Moreover, Delta SEM may be configured to provide a landing energy from a range of 10 eV to 1 keV, 100 eV to 1 keV, 100 eV to 500 eV, 50 eV to 500 eV, or 50 eV to 400 eV. One or more sides of the area of the measured surface of the sandwiched sample including the blocks of a semiconductor material may be, for example, 0.75 cm, 1 cm, 1.25 cm, 1.5 cm, 1.75 cm, or 2 cm in length. The area of the measured surface may be rectangular or square-shaped, and may have sizes of a different length, e.g. 1 cm×2 cm. The width and/or length may be at least 1 cm. The surface area allows for the surface charge distribution and charging issues to be minimized.

Using the present method, the issue of field distortion issue which is particularly common in SEM imaging in low energy can be resolved.

The blocks of a semiconductor material may be formed by stacking chips of the semiconductor material, adhering the chips of the semiconductor material using an adhesive, or adhering the chips of the semiconductor material using an epoxy adhesive.

Polishing of the sandwiched sample may be performed using any polishing method to achieve a mirror surface with none or very minimal surface scratches. For example, polishing can be performed using diamond paper and water. Mirror polishing may be performed as an additional step. The polishing may be carried out as a mechanical polishing.

Measuring the surface of the sandwiched sample may include one or more of acquiring an image of the processed semiconductor sample, and comparing the acquired image with a reference.

The method may further include determining defects in the processed semiconductor sample. Determining defects may be performed by determining defects from an image, or determining defects based on comparing acquired images with the reference.

Acquiring the image may include acquiring the image by multiple beam-scanning electron microscopy. Multi-beam scanning electron microscopy allows to obtain high resolution images in short time. The reference may be selected form the group consisting of design data, a reference wafer and a reference chip.

According to another embodiment, a device for semiconductor sample inspection or analysis is provided, including: a sample stage including two blocks of semiconductor material for sandwiching a semiconductor sample; a polishing device configured to polish the surface of the sandwiched processed semiconductor sample, and a measuring device configured to measure the surface of the sandwiched processed semiconductor sample.

The measuring device may include one or more of a multi-beam scanning electron microscope, a scanning electron microscope (SEM), and a Delta SEM microscope. The landing energy may be in the range of 10 eV to 1 keV, 100 eV to 1 keV, 100 eV to 500 eV, 50 eV to 500 eV, or 50 eV to 400 eV.

The device may further includes an evaluation device configured to evaluate the data obtained from the measuring device.

The polishing device may be configured to perform one or more of standard polishing, grinding and polishing, and mirror-polishing.

The device may be configured to perform any of the methods discussed above.

The above summary is merely intended to give a brief overview over some possible implementations and is not to be construed as limiting in any way.

DETAILED DESCRIPTION

In the following, various embodiments will be described in detail referring to the attached drawings. These embodiments are to be understood as examples only and are not to be construed as limiting in any way.

Features from different embodiments may be combined to form further embodiments. Variations or modifications described with respect to one of the embodiments may also be applicable to other embodiments and will therefore not be described repeatedly.

Embodiments as discussed herein may be employed for wafer inspection in photolithography. A method for inspecting a semiconductor sample is illustrated in FIG. 1.

Embodiments as discussed herein may be employed for metrology wafer inspection in the context of manufacturing, development or analysis of semiconductor devices. An example for such a manufacturing of semiconductor devices as an application environment for various embodiments is illustrated in FIG. 1.

Figure 1:
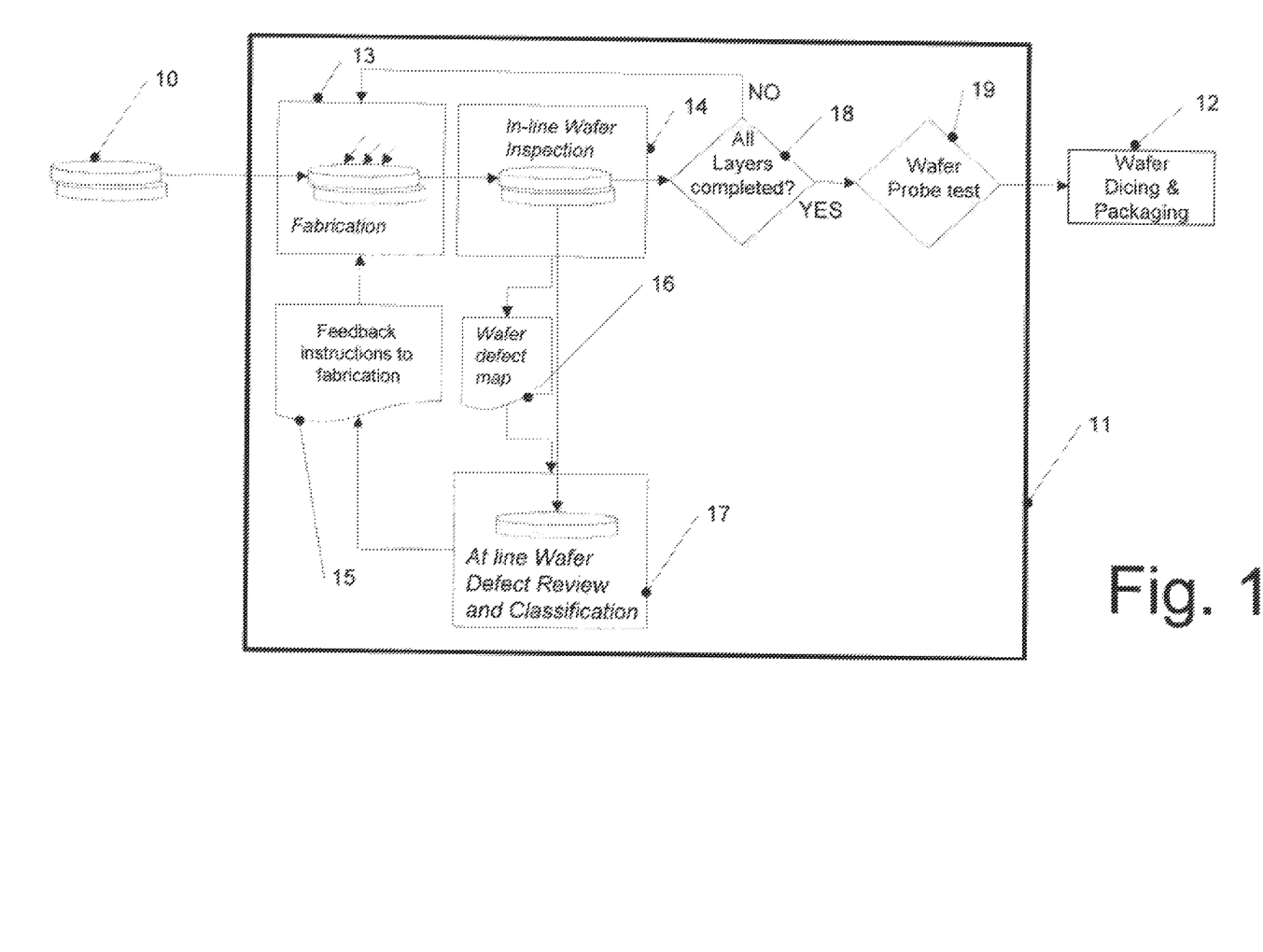
FIG. 1 is a chart illustrating an application environment for some embodiments, in which cross-sectional analysis can be applied using techniques disclosed herein.

In FIG. 1, the manufacturing of semiconductor devices starts with blank wafers 10. Examples for such blank wafers 10 include silicon wafers or gallium arsenide wafers, but any semiconductor wafers or other substrates used for semiconductor device manufacturing may be used. First, the wafers 10 are subjected to a so-called front-end processing at 11. Front-end processing relates to all processing steps where structures are formed on or in the wafer, before the structures on the wafers are mechanically separated from each other. For mass production, of a plurality of equal structures is formed on the wafers, which are then separated into separate semiconductor devices. Wafers 10 in front-end processing 11 are subjected to a plurality of fabrication steps 13. Such fabrication steps may include etching, layer deposition of semiconductor layers or metal layers, diffusion or implantation, for example for doping, cleaning, wafer planarization, resist coating and resist treatment, lithography exposure etc. With these fabrication steps, structures are formed on wafers 10.

After certain fabrication steps, the wafers may be subjected to in-line wafer inspection at 14. In the in-line wafer inspection, methods and devices are used to obtain a defect map 16 of the wafer, i.e. to obtain information where on the wafer structures have not been formed as desired.

An at-line wafer defect review and classification at 17 can also be performed. "At-line" indicates that the wafers in this case are taken out of the usual production process for further inspection. In particular, in the review at 17, the indications of process variations or defects may be reviewed in order to verify and classify. As a result, at 15 feedback instructions to the fabrication may be given, for example to modify fabrication parameters to counter process variations, or also instructions for example to do maintenance due to possible malfunctioning components in a corresponding fabrication device. The wafer or semiconductor may be analyzed via cross-sectional analysis using techniques disclosed herein, i.e. a sample may be cut out of the semiconductor and subjected to measurement conditions. Moreover, the wafer can be evaluated by acquiring an image of the cross-sectional sample of the wafer. In this respect, by techniques disclosed herein, coupon analysis may be used for analysis and inspection to analyze the cross-section of a test coupon provided on the wafer.

These steps are repeated until at 18 all layers of the front-end processing are completed. Following this, at 19 wafer probe testing may be performed, where for example structures on the wafer are contacted electrically by probes to perform test measurements. This concludes the front-end processing.

After the front-end processing at 11, back-end processing 12 follows where the wafers are diced into separate chips, and the chips are packaged. More testing of the semiconductor devices manufactured may occur during the back-end processing 12.

It should be noted that techniques disclosed herein may be used as an addition to in-line wafer inspection by analyzing coupons or other structures on wafers, but may also be used in other cases where a cross-section, e.g. a layer structure, of a processed semiconductor wafer or parts thereof (e.g. diced wafers) needs to be examined. Examples may include development of semiconductor devices or error analysis of faulty semiconductor devices.

In accordance with the SEM inspection method, a defect present in a circuit pattern is detected by scanning a surface of a wafer formed with a circuit pattern with an electron beam focused onto a spot and comparatively inspecting obtained SEM images. By using the SEM defect inspection of a circuit pattern, extremely small etching residues and pattern defects which are not more than the resolution of an optical microscope and electric defects such as faulty openings of extremely small connection holes can be detected.

Delta SEM with Cs/Cc correctors (which correct aberrations) differentiates from other available SEM techniques with its ultra low landing energy, enhanced material contrast and high resolution. However, for SEM cross sectioned sample analysis which is involved in semiconductor analysis labs, according to the prior art, cross sectioned samples mounted on a conventionally employed metal stub holder can only work on the landing energy above 500V, with verified data at landing energy at 800V due to the field distortion issue.

FIGS. 2-6 illustrate methods and devices according to embodiments.

Figure 2:
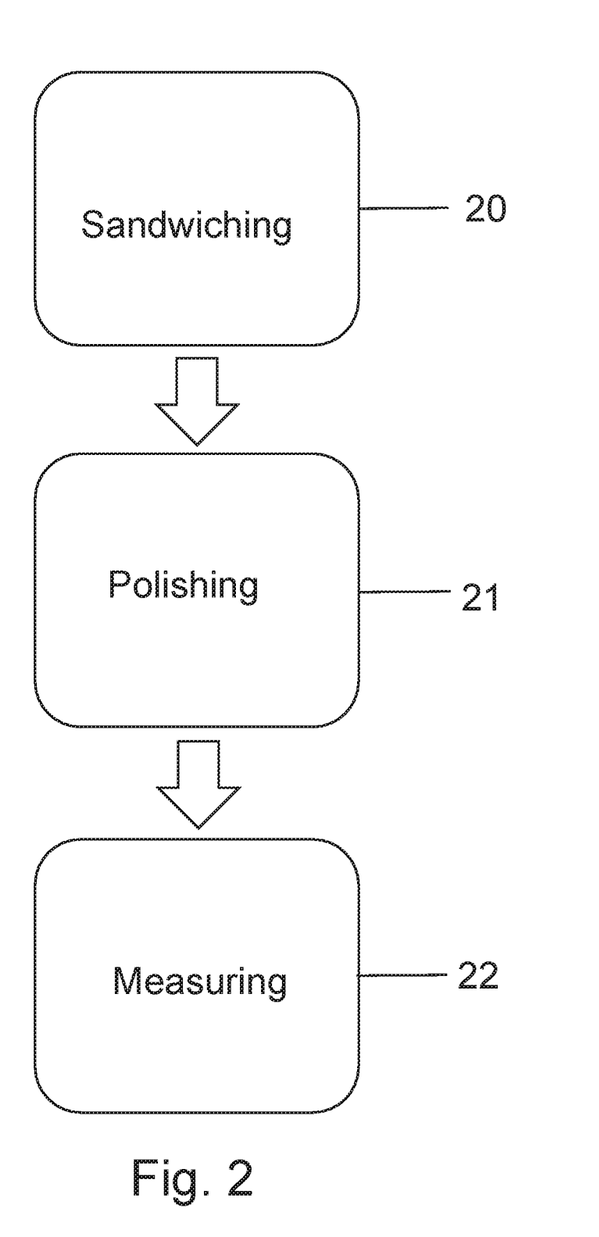
FIG. 2 is a flowchart illustrating an embodiment of the method.

FIG. 2 is a flowchart of an embodiment of the method which includes the step 20 of sandwiching a processed semiconductor sample between two blocks of a semiconductor material, the step 21 of polishing the sandwiched sample, and the step 22 of measuring at the polished sample surface of the sample.

Figure 3:
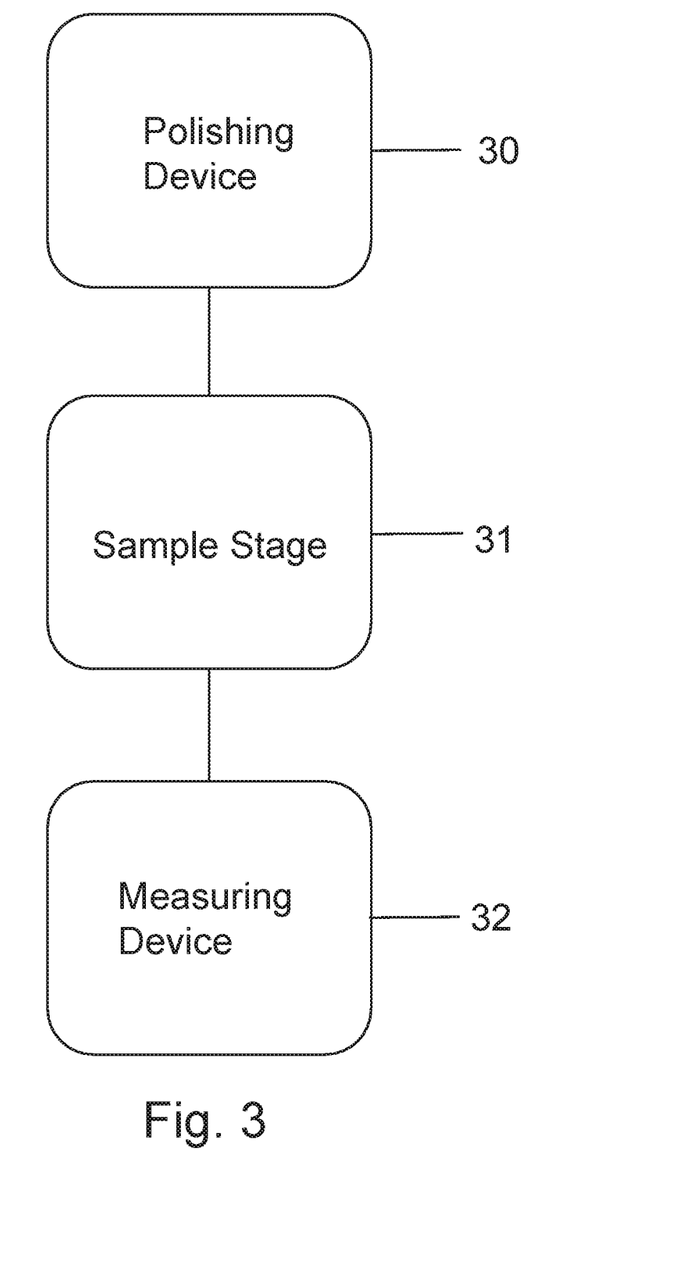
FIG. 3 is a chart illustrating an embodiment of the device.

FIG. 3 is an exemplary arrangement of the device for semiconductor sample inspection or analysis, including a sample stage 30, a polishing device 31, and a measuring device 32.

Figure 4:
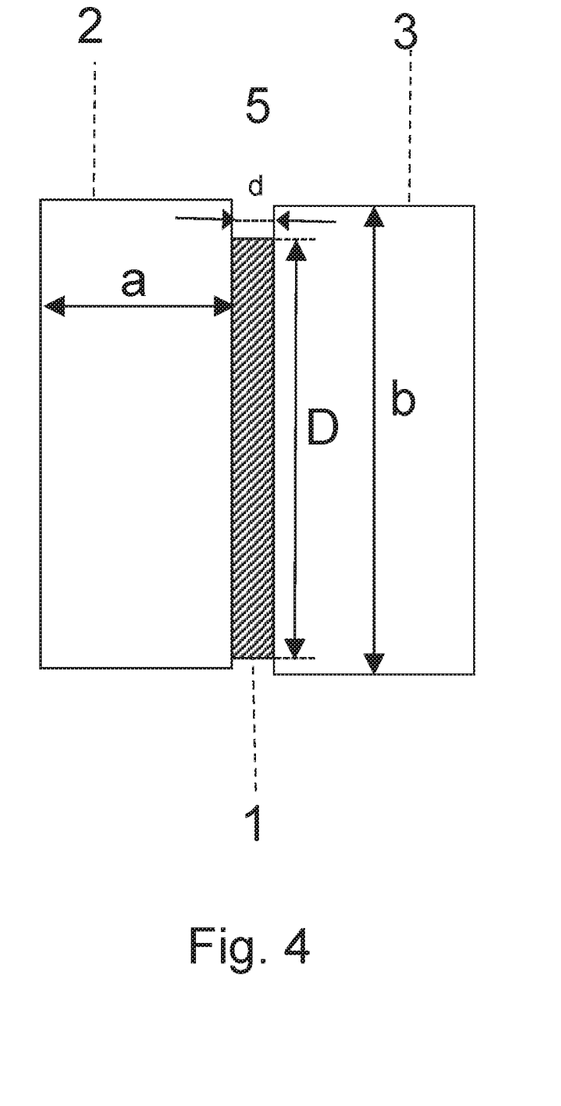
FIG. 4 is a surface view illustrating an embodiment of the method wherein a semiconductor sample such as a Si wafer sample has been sandwiched between two blocks of the same semiconductor material, before the step of polishing.
Figure 5:
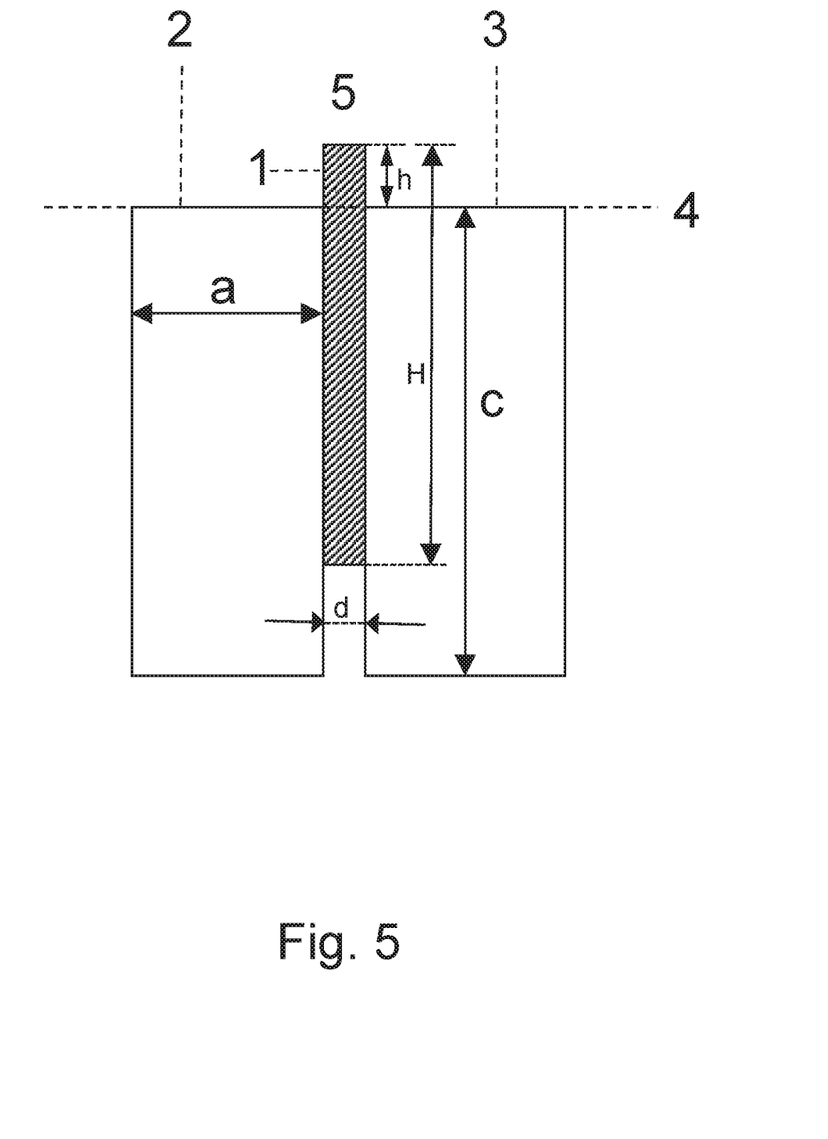
FIG. 5 is a side view of an embodiment of the method wherein a semiconductor sample such as a Si wafer sample has been sandwiched between two blocks of the same semiconductor material, before the step of polishing.
Figure 6:
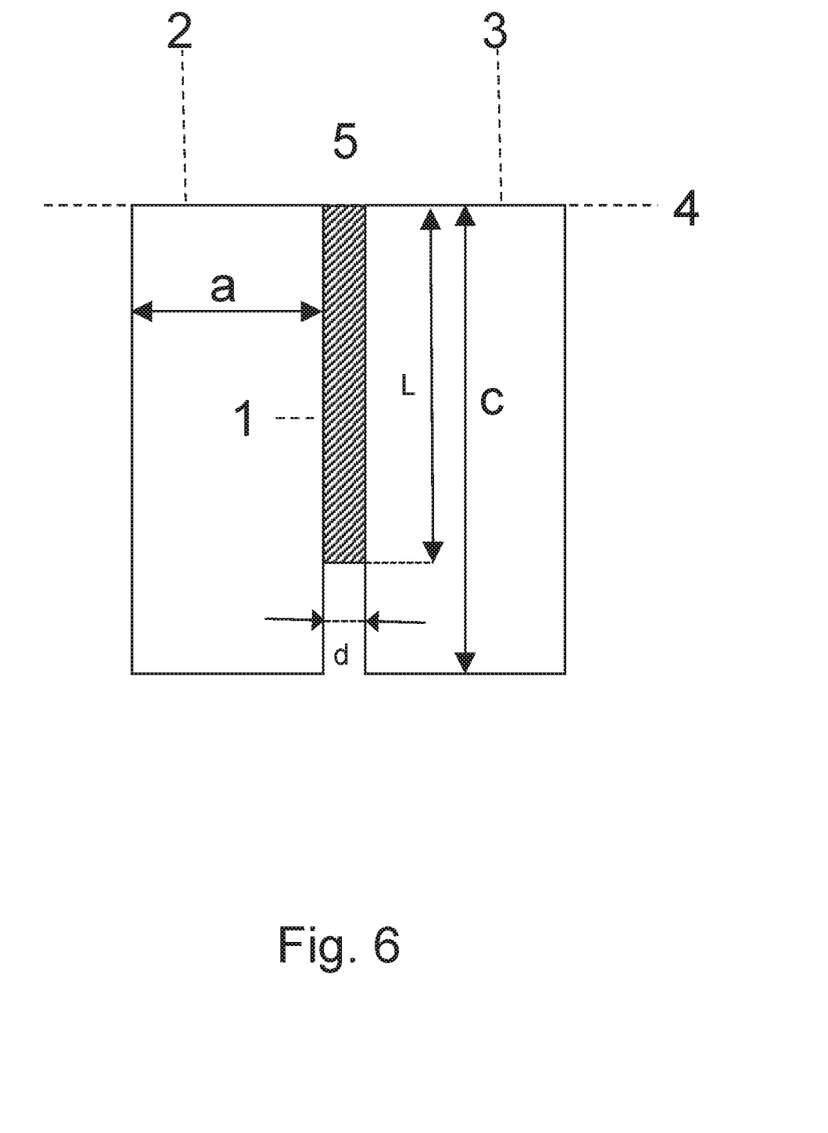
FIG. 6 is a side view of an embodiment of the method wherein a semiconductor sample such as a Si wafer sample has been sandwiched between two blocks of the same semiconductor material after the step of polishing.

FIG. 4 is a surface view illustrating an embodiment wherein a processed semiconductor sample 1 such as a processed Si wafer sample, which is shown in FIGS. 4 to 6 as a hatched area, has been sandwiched between two blocks 2, 3 of the semiconductor material. In the illustrated case, the blocks of a semiconductor material 2, 3 have a thickness a. The sandwiched semiconductor sample which has a thickness d is shown in a state prior to the polishing step. In this example the Si blocks 2 and 3 have a depth b which is larger than the depth D of the processed semiconductor sample 1, i.e. there is a gap d between the semiconductor sample 1 and the blocks 2, 3 such that in the example illustrated in FIG. 4, the blocks are larger in thickness indicated by the parameter a than the thickness of the processed semiconductor Si sample which is indicated as thickness d. The semiconductor sample 1 is inserted with the side surface d being arranged towards the top of the sandwiched sample. The side surface 5 may be the surface which has not been printed in a photolithographic printing step. Furthermore, in the embodiment illustrated in FIG. 4, the processed semiconductor sample 1 can be a Si wafer or a part thereof that has been fixed between the two blocks 2, 3 of the same semiconductor material, such that in the illustrated example the blocks are Si blocks. The blocks can be prepared by stacking chips of the semiconductor material, fixing the chips, for example using an adhesive, and thus forming the blocks of the same semiconductor material. In an exemplary case, referring to the embodiment illustrated in FIG. 4, the blocks 2, 3 are made of Si.

FIG. 5 is a side view of an embodiment of the method. Moreover, FIG. 5 may illustrate a side view of the example illustrated in FIG. 4. Again, as in the case of FIG. 4, the processed semiconductor sample 1 in FIG. 5 is shown as a cross sectioned Si coupon sample that is sandwiched between two blocks 2, 3 of the same semiconductor material (i.e. in this exemplary case, Si) before polishing. As can be seen from the side view in FIG. 5, in this example the processed semiconductor sample protrudes with the distance h over the surface 4 formed by the two blocks 2, 3. The sample can be inserted under visual inspection to be aligned with the blocks such as to have little protrusion above the upper surface formed by the blocks. Alternatively, the sample can be plunged into the two blocks thus preparing for later alignment of the blocks by polishing the blocks such as to form an even surface with the sample.

In the example of FIG. 5, the part having a height h of the part of the semiconductor sample 1 is the part which extends beyond the surface 4 given by the blocks 2, 3 and is the amount that will be removed by the subsequent step of polishing in order to form an even surface with the two blocks 2, 3 of the same semiconductor material along the line 4 shown in FIG. 5, i.e. the alignment level for the even surface to be produced in the polishing step. Hence, as in the case of FIG. 4, FIG. 5 illustrates an embodiment before the step of polishing. Again, it can be seen in this illustrated example that the blocks of the same semiconductor material 2, 3 may have dimensions that are greater or smaller in size than those of the processed semiconductor sample, which is sandwiched in between the blocks. As an example, the thickness a of the blocks 2, 3 may be greater than the thickness d of the processed semiconductor sample 1, and the depth b of the blocks 2, 3 may be larger than the depth D of the processed semiconductor sample 1. In another example, the sample is positioned below the surface 4 formed by the blocks, i.e. the sample can be plunged into the block.

FIG. 6 is a side view of the Si coupon sample of FIG. 4 and FIG. 5 after polishing. The surface of the sample has been levelled during the alignment line 4 such that no protrusion is formed out of the surface formed by the two blocks, i.e. an even surface is formed in an alignment with the surface of the two blocks 2, 3 along the level 4. After the polishing step, the processed semiconductor sample 1 has a reduced height (L in FIG. 4) which is reduced by an amount (h in FIG. 6) that has been removed by polishing from an original height (H in FIG. 6). Following the polishing step, the polished surface 5 is subjected to the measuring step. For example, the measurement can be made at the surface of the polished sample such that the blocks are not part of the measured surface. In an example, a mirror-polishing step on the aligned surface 4 can be performed. The polishing may be mechanical polishing. Measuring of the sample at the polished surface 5 can be performed using a measuring device. In an example, the step measuring includes using multi-beam scanning electron microscopy. In particular, multi-beam scanning electron microscopy may be Delta SEM microscopy.

The use of Delta SEM allows for low landing energy which enables minimal electron beam caused irradiation damage on Si samples without compromising the spatial resolution, also provides much enhanced material contrast. Moreover, using the present method, field distortion is minimized or avoided. This is the one of the most desirable features for Delta SEM in semiconductor device structural analysis.

In an exemplary embodiment, two Si blocks 2, 3 measured at least 5 mm thick (i.e. a is 5 mm or greater) are stacked up using multiple Si chips of the desired sizes—to provide a block that has a length (c in FIG. 5) which is greater than the thickness d of the sandwiched sample, and a height b which is wider than the length D of the cross sectioned sample 1. Then the cross sectioned processed semiconductor sample 1 is sandwiched in between of the two blocks 2, 3. In an example, Si chips and the sample are adhered together with Si blocks 2, 3. In an example, the chips are fixed. The chips may be adhered using a glue or an adhesive. The adhesive can be applied in an even manner, and as a very thin film. The adhesive may be any type which is effective in adhering the semiconductor material, and may be an adhesive including a compound such as an epoxy adhesive.

Performing a method in this way, the surface charge distribution and charging issues are minimized, and the distortion issue is resolved. In an example, the measuring step was carried out using Delta SEM as multi-beam scanning electron microscopy.

A good resolution and material contrast image can be easily obtained in the low landing energy range 10 eV to 1 keV, 100 eV to 1 keV, 100 eV to 500 eV, 50 eV to 500 eV, or 50 eV to 400 eV.

The SEM data have shown sharp material contrast close to TEM images, also a clear interface of different materials meeting the expected resolution.

In one embodiment, the cross sectioned sample is sandwiched between two Si blocks, and the length of one or more sides of the polished surface area is larger than 1 cm to ensure a good homogeneous surface. In an example, the area of the polished surface is larger than 1 cm×1 cm. Using Delta SEM, such enough surface area leads to a particularly beneficial effect in avoiding field distortion.

The blocks sandwiching the processed semiconductor sample include the same material as the processed semiconductor sample. In an embodiment, the sample is Si and the sandwiching blocks are made of Si. In an example, the sandwiching blocks are of homogeneous Si which has the same material property as the Si used in the processed semiconductor sample which is sandwiched in-between.

In an example, semiconductor blocks can be stacked together using Si chips with epoxy adhesive, or other ways as long as the two Si blocks exhibit substantially the same material as the processed semiconductor sample.

In an example, the processed semiconductor sample is a cross sectioned sample and is sandwiched between two Si blocks. For a good homogeneous surface, the length of one or more sides of the polished entire surface area may be larger than 1 cm such as to form a surface area large enough to counter the field distortion issue. For example, the area of the polished surface may be 1 cm×1 cm.

In an exemplary embodiment, two Si blocks may be stacked together using Si chips with an adhesive, or other ways so long the two Si blocks exhibit the same Si homogeneity as the cross sectional semiconductor sample. The Si blocks may be commercially available Si blocks or stacked up Si chips.

In an embodiment shown in FIG. 6, a device is provided which includes a sample stage 30 including two blocks of semiconductor material for sandwiching a semiconductor sample, a polishing device 31 configured to polish the surface of the sandwiched processed semiconductor sample, and a measuring device 32 configured to measure the surface of the sandwiched processed semiconductor sample. The sample stage 30 may have any form which is suitable to place the sample for inspection. The polishing device 31 may be of any form which allows for polishing the sample. In an example, the device may be a standard lab grinding and polishing system.

In an example, polishing can be achieved using one or more of diamond paper, water, a polishing liquid, and a water jet.

Furthermore, the polishing device 31 may be configured to perform polishing at different speeds Moreover, the polishing device may be configured to perform mirror polishing.

The device may be configured to perform the method. The device may provide a sample stage 31 which the sample of a processed semiconductor shown in FIGS. 4 to 6 can be placed and sandwiched. Using the step of polishing using polishing device 31, the polished surface 5 has been formed by polishing to achieve the aligned surface 4 between the processed semiconductor sample 1 and the blocks 2, 3. Furthermore, the device includes a measurement device 32 to perform the step of measuring at the surface of the sample.

In an embodiment, the device may include a multi-beam scanning electron microscope as the measuring device 32. In an example, the device includes a Delta SEM microscope.

The method may include performing an image acquisition of a wafer to be inspected. To this end, the device may include an image acquisition device. The term "image", as used herein, is to be construed broadly and encompasses all data which may represent structures formed on the wafers in an array of image elements. The kind of imaging needed may also depend on the size of the structures on the wafer, as for smaller structures higher resolution techniques are needed. In particular, image acquisition devices may be arranged within the frame of Delta SEM.

This image may then be processed further. To achieve this, an evaluation device can be provided. The evaluation device may be a computer or similar device having a processor programmed accordingly, for example a desktop computer, a laptop, a tablet PC or the like. In other embodiments, parts or all of the method may be implemented using specific hardware like application specific integrated circuits (ASICs) or field programmable gate arrays (FPGAs). Generally, any device capable of performing the processing may be used.

Furthermore, a reference for the wafer may be provided. In some embodiments, this reference may include design data, i.e. data representing how the wafer was designed to look like in each processing stage. This may be in the form of a computer-aided design (CAD) file, for example a file in the GDSII (graphical design station/graphic data system II) format or OASIS (open artwork system interchange standard) format.

The following numbered examples demonstrate one or more aspects of the disclosure.

Example 1. A method for inspection or analysis of a processed semiconductor sample includes sandwiching a processed semiconductor sample between two blocks of a semiconductor material, polishing the sandwiched sample such that an even surface is obtained, and measuring at the polished surface of the sample. The blocks of a semiconductor material includes the same semiconductor material as the semiconductor sample.

Example 2. The method of Example 1, wherein the processed semiconductor sample is one or more of a sample of a wafer, a Si or GaAs wafer or a part thereof, a semiconductor that has been exposed in a photolithography process, and a Si or GaAs wafer, a SOI wafer, a coupon wafer, or a part thereof that has been exposed in a photolithography process.

Example 3. The method of Examples 1-2 or any combination thereof, wherein the inspection or analysis includes one or more of an inspection during a wafer production process, coupon level wafer inspection, coupon wafer analysis, or at-line inspection during a wafer production process.

Example 4. The method of Examples 1-3 or any combination thereof, wherein the surface includes a side surface of the semiconductor sample.

Example 5. The method of Examples 1-4 or any combination thereof, wherein the surface includes a side surface of the processed semiconductor sample, and sandwiching a processed semiconductor sample includes fixing the sample between the two blocks of semiconductor material, fixing the processed semiconductor sample between the two blocks of a semiconductor material using an adhesive, or fixing the processed semiconductor sample between the two blocks of a semiconductor material using an epoxy adhesive.

Example 6. The method of Examples 1-5 or any combination thereof, wherein the blocks of a semiconductor material are larger in size than the semiconductor sample, or wherein the thickness of each block of semiconductor material is about 5 mm, about 6 mm, about 7 mm, or in a range of 5-10 mm.

Example 7. The method of Examples 1-6 or any combination thereof, wherein measuring the surface of the sandwiched sample includes measuring by multi-beam scanning electron microscopy.

Example 8. The method of Example 7, wherein multi-beam scanning electron microscopy includes Delta SEM.

Example 9. The method of Example 8, wherein the Delta SEM is configured to provide a landing energy from 10 eV to 1 keV, 100 eV to 1 keV, 100 eV to 500 eV, 50 eV to 500 eV, or 50 eV to 400 eV.

Example 10. The method of Examples 1-9 or any combination thereof, wherein one or more sides of the area of the measured surface of the sandwiched sample including the blocks of a semiconductor material is at least 0.75 cm, 1 cm, 1.25 cm, 1.5 cm, 1.75 cm, or 2 cm in length, or wherein the area of the measured surface of the sandwiched sample is at least 1 cm×1 cm.

Example 11. The method of Examples 1-10 or any combination thereof, further including one or more of forming the blocks of a semiconductor material by stacking chips of the semiconductor material, adhering the chips of the semiconductor material using an adhesive, or adhering the chips of the semiconductor material using an epoxy adhesive.

Example 12. The method of Examples 1-11 or any combination thereof, wherein polishing of the sandwiched includes one or more of mechanical polishing, polishing using diamond paper and water, or mirror-polishing.

Example 13. The method of Examples 1-12 or any combination thereof, wherein measuring the surface of the sandwiched sample includes one or more of acquiring an image, acquiring an image of the processed semiconductor sample, and comparing the acquired image with a reference.

Example 14. The method of Example 13, further including determining defects in the processed semiconductor sample from an image, or determining defects based on comparing acquired images with the reference.

Example 15. A device for semiconductor sample inspection or analysis, includes a sample stage including two blocks of semiconductor material for sandwiching a semiconductor sample, a polishing device configured to polish the surface of the sandwiched processed semiconductor sample, and a measuring device configured to measure the surface of the sandwiched processed semiconductor sample.

Example 16. The device of Example 15, wherein the measuring device includes one or more of a multi-beam scanning electron microscope, a SEM microscope, or a Delta SEM microscope, or a Delta SEM microscope configured to provide a landing energy in a range of 10 eV to 1 keV, 100 eV to 1 keV, 100 eV to 500 eV, 50 eV to 500 eV, or 50 eV to 400 eV.

Example 17. The device of Examples 15-16 or any combination thereof, wherein the device further includes an evaluation device configured to evaluate the data obtained from the measuring device.

Example 18. The device of Example 15-17 or any combination thereof, wherein the Delta SEM microscope is configured to provide a landing energy in a range of 10 eV to 1 keV, 100 eV to 1 keV, 100 eV to 500 eV, 50 eV to 500 eV, or 50 eV to 400 eV.

Example 19. The device of Example 15-18 or any combination thereof, wherein the polishing device is configured to perform one or more of standard polishing, mechanical polishing, grinding and polishing, and mirror-polishing.

Example 20. The device of Examples 15-19 or any combination thereof, wherein the device is configured to perform the method of Examples 1-14.

Various examples of the disclosure have been described. Any combination of the described systems, operations, or functions is contemplated. These and other examples are within the scope of the following claims.

As can be seen from the above explanations, numerous variations and modifications are possible, and it is evident that the scope of the present application is not limited by the specific embodiments.

What is claimed is:

1. A method, comprising:
sandwiching a processed semiconductor sample between two blocks of a semiconductor material;
polishing the sandwiched sample to obtain a polished, even surface; and
measuring the polished, even surface of the sample,
wherein the blocks of a semiconductor material comprise the same semiconductor material as the semiconductor sample, and the polished, even surface comprises a side surface of the semiconductor sample.

2. The method of claim 1, wherein the processed semiconductor sample comprises at least one member selected from the group consisting of a sample of at least a part of a wafer and a semiconductor that has been exposed in a photolithography process.

3. The method of claim 1 comprising at least one member selected from the group consisting of inspection during a wafer production process, coupon level wafer inspection, coupon wafer analysis, at-line inspection during a wafer production process, and inspection during a photolithography production process.

4. The method of claim 1, wherein:
sandwiching a processed semiconductor sample comprises at least one member selected from the group consisting of fixing the sample between the two blocks of semiconductor material, fixing the processed semiconductor sample between the two blocks of a semiconductor material using an adhesive, and fixing the processed semiconductor sample between the two blocks of a semiconductor material using an epoxy adhesive.

5. The method of claim 1, wherein at least one of the following holds:
the blocks of a semiconductor material have dimensions which are larger than the dimensions of the semiconductor sample; and
the thickness of each block of semiconductor material is at least 5 mm.

6. The method of claim 1, wherein measuring the polished, even surface of the sandwiched sample comprises measuring by multi-beam scanning electron microscopy.

7. The method of claim 6, wherein multi-beam scanning electron microscopy comprises Delta SEM.

8. The method of claim 7, wherein the Delta SEM is configured to provide a landing energy from 10 eV to 1 keV.

9. The method of claim 1, wherein at least one side of an area of the measured surface of the sandwiched sample comprising the blocks of a semiconductor material is at least 0.75 cm.

10. The method of claim 1, further comprising at least one member selected from the group consisting of forming the locks of a semiconductor material by stacking chips of the semiconductor material, adhering the chips of the semiconductor material using an adhesive, and adhering the chips of the semiconductor material using an epoxy adhesive.

11. The method of claim 1, wherein polishing of the sandwiched comprises at least one member selected from the group consisting of mechanical polishing, polishing using diamond paper and water, and mirror-polishing.

12. The method of claim 1, wherein measuring the surface of the sandwiched sample comprises at least one member selected from the group consisting of acquiring an image, acquiring an image of the processed semiconductor sample, and comparing the acquired image with a reference.

13. The method of claim 12, further comprising determining defects in the processed semiconductor sample from the image, or determining defects based on comparing acquired images with the reference.

14. A device, comprising:
a sample stage comprising two blocks of semiconductor material configured to sandwich a semiconductor sample;
a polishing device configured to polish the surface of the sandwiched processed semiconductor sample; and
a measuring device configured to measure the surface of the sandwiched processed semiconductor sample,
wherein the polished, even surface comprises a side surface of the semiconductor sample.

15. The device of claim 14, wherein the measuring device comprises at least one member selected from the group consisting of a multi-beam scanning electron microscope, a SEM microscope, and a Delta SEM microscope.

16. The device of claim 15, wherein the measuring device comprises a Delta SEM microscope configured to provide a landing energy in a range of 10 eV to 1 keV.

17. The device of claim 14, further comprising an evaluation device configured to evaluate the data obtained from the measuring device.

18. The device of claim 14, wherein the polishing device is configured to perform wherein the measuring device comprises standard polishing, grinding and polishing, and mirror-polishing.

19. A method, comprising:
polishing a sandwiched sample to obtain a polished, even surface, the sandwiched sample comprising a processed semiconductor sample between two blocks of a semiconductor material; and
measuring the polished, even surface of the sample,
wherein the blocks of a semiconductor material comprise the same semiconductor material as the semiconductor sample, and the polished, even surface comprises a side surface of the semiconductor sample.

* * * * *